United States Patent [19]

Smith et al.

[11] Patent Number: 4,806,699
[45] Date of Patent: Feb. 21, 1989

[54] PROCESS FOR THE PRODUCTION OF AROMATIC HYDROCARBONS INCORPORATING BY-PRODUCT UTILIZATION

[75] Inventors: David J. H. Smith, Camberley; William T. Woodfin, Hook, both of England

[73] Assignee: The British Petroleum Company p.l.c., London, England

[21] Appl. No.: 117,237

[22] Filed: Nov. 5, 1987

[30] Foreign Application Priority Data

Nov. 6, 1986 [GB] United Kingdom ................ 8626532

[51] Int. Cl.$^4$ .................................................. C07C 2/84
[52] U.S. Cl. ..................................... 585/314; 585/407; 585/415; 585/417; 585/419
[58] Field of Search ............... 585/312, 314, 302, 301, 585/407, 415, 417, 419

[56] References Cited

U.S. PATENT DOCUMENTS

| | | | |
|---|---|---|---|
| 3,827,867 | 8/1974 | Heinemann et al. | 585/415 |
| 4,413,153 | 11/1983 | Garwood et al. | 585/312 |
| 4,528,412 | 7/1985 | Steacy | 585/415 |
| 4,642,402 | 2/1987 | Jensen | 585/415 |
| 4,654,458 | 3/1987 | Jezl et al. | 585/415 |
| 4,677,235 | 6/1987 | Mowry | 585/417 |
| 4,684,758 | 8/1987 | Derr, Jr. et al. | 585/314 |

FOREIGN PATENT DOCUMENTS

| | | |
|---|---|---|
| 0050021 | 4/1982 | European Pat. Off. |
| 0119023 | 9/1984 | European Pat. Off. |
| 0119027 | 9/1984 | European Pat. Off. |
| 0147111 | 7/1985 | European Pat. Off. |
| 0162636 | 11/1985 | European Pat. Off. |
| 0164864 | 12/1985 | European Pat. Off. |
| 0163385 | 12/1985 | European Pat. Off. |
| 0169743 | 1/1986 | European Pat. Off. |
| 0178853 | 4/1986 | European Pat. Off. |
| 0186949 | 7/1986 | European Pat. Off. |
| 0202000 | 11/1986 | European Pat. Off. |
| 0211577 | 2/1987 | European Pat. Off. |
| 0215579 | 3/1987 | European Pat. Off. |
| 0232962 | 8/1987 | European Pat. Off. |
| 1499199 | 1/1978 | United Kingdom |
| 1537780 | 1/1979 | United Kingdom |
| 1561590 | 2/1980 | United Kingdom |

*Primary Examiner*—Asok Pal
*Attorney, Agent, or Firm*—Brooks Haidt Haffner & Delahunty

[57] ABSTRACT

Aromatic hydrocarbons are produced from a feedstock comprising ethane and/or propane and/or butane by the steps of:

(A) reacting the feedstock in the presence of a dehydrocyclodimerization catalyst to produce a product comprising aromatic hydrocarbons, hydrogen and methane, (B) separating the product of step (A) into an aromatic hydrocarbon fraction, a methane-rich gaseous fraction and a hydrogen-rich gaseous fraction, (C) feeding all or part of the methane-rich gaseous fraction separated in step (B) to a synthesis gas production unit, thereby to produce synthesis gas, and (D) contacting the synthesis gas from step (C) together with all or part of the hydrogen-rich gaseous fraction separated in step (B), thereby increasing the hydrogen to carbon monoxide ratio of the synthesis gas, with a Fischer-Tropsch conversion catalyst to produce a hydrocarbon product.

16 Claims, 1 Drawing Sheet

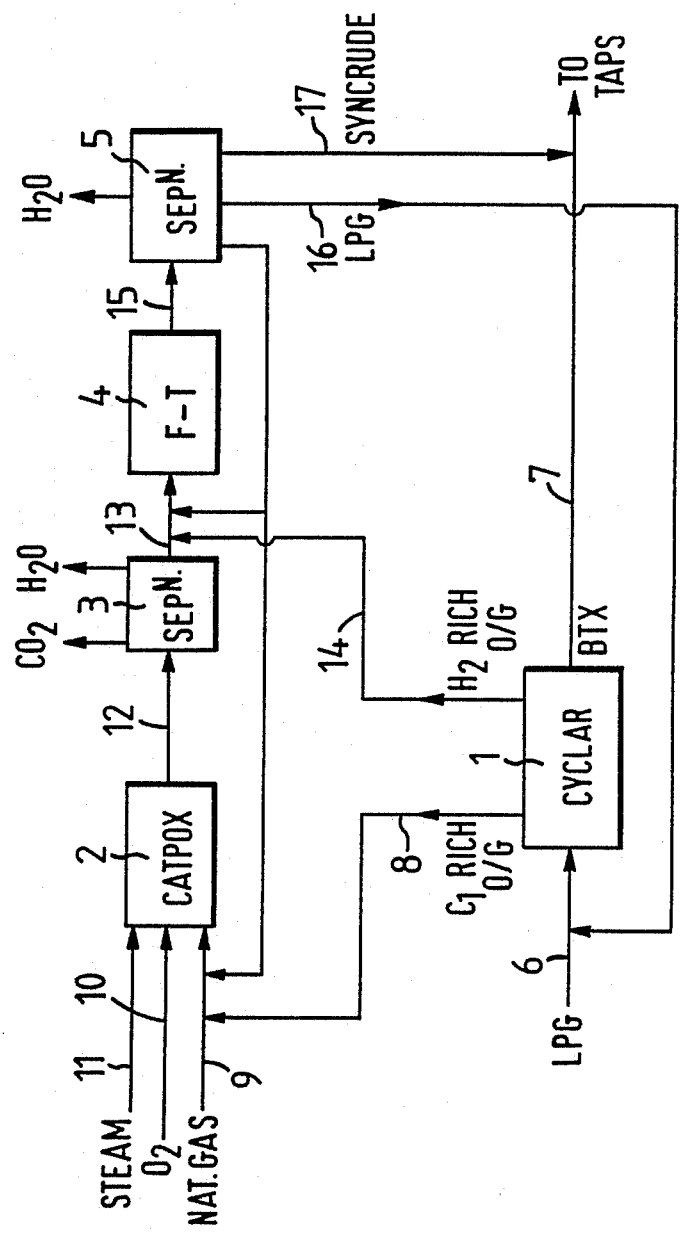

PROCESS FOR THE PRODUCTION OF AROMATIC HYDROCARBONS INCORPORATING BY-PRODUCT UTILIZATION

The present invention relates in general to the production of aromatic hydrocarbons and in particular to a process for the production of aromatic hydrocarbons by the catalysed conversion of a $C_2$–$C_4$ hydrocarbon feedstock in which by-products are utilised in the production of useful hydrocarbon products.

The catalysed production of aromatic hydrocarbons such as benzene, toluene and xylene by the catalysed conversion of a $C_2$–$C_4$ hydrocarbon feedstock, sometimes referred to as dehydrocyclodimerisation (DHCD), has been known for some time. One form of the process in which $C_2$–$C_4$ hydrocarbons are converted to aromatic hydrocarbons over a gallium loaded zeolite catalyst is rapidly gaining recognition as the BP Cyclar process. In addition to aromatic hydrocarbons the process generates, as by-products, a methane-rich stream and a hydrogen-rich stream, which in the absence of any other use for these products represent a loss to the process.

Although the $C_2$–$C_4$ hydrocarbon feedstock may be derived from other sources, for example by-product refinery streams, a potential source of such feedstock is Liquid Petroleum Gas (LPG) obtained by separating methane from natural gas, which though its detailed composition may vary according to its source, principally comprises methane, ethane, propane and butane together with minor amounts of one or more of carbon dioxide, nitrogen and $C_4^+$ hydrocarbons. A potential use of the large volumes of recovered methane is as feedstock for conversion into synthesis gas by a variety of routes, followed by conversion of the synthesis gas so-produced into higher value products, such as for example methanol, higher alcohols, or hydrocarbons by the well-known Fischer-Tropsch (FT) conversion.

The production of hydrocarbons from methane or methane-containing mixtures, for example natural gas, by an initial conversion into synthesis gas by, for example, either steam reforming, autothermal reforming or partial oxidation, followed by conversion over a Fischer-Tropsch catalyst is by now recognised in the art. Whichever route is used for the generation of synthesis gas, it is generally necessary to adjust its hydrogen to carbon monoxide ratio to a value which is optimum for subsequent Fischer-Tropsch conversion into hydrocarbons. The oxidative routes, having a maximum hydrogen to carbon monoxide ratio of 2:1, require an increase in the hydrogen to carbon monoxide ratio. For this purpose a shift reaction involving the production of hydrogen by the reaction of steam with a portion of the carbon monoxide generated by the synthesis gas production process is generally postulated. The shift reaction also produces carbon dioxide which is generally undesirable in the subsequent Fischer-Tropsch reaction and generally requires a step for its removal, together with carbon dioxide generated in the synthesis gas production step and steam. The inclusion of a shift reaction step and a possible carbon dioxide removal step detract from the economics of the process both in terms of capital expenditure in plant and loss of overall productivity through carbon loss.

We have now developed a process which integrates the two previously known processes in a manner which is mutually beneficial to their simultaneous operation.

Accordingly, the present invention provides a process for the production of aromatic hydrocarbons from a feedstock comprising ethane and/or propane and/or butane which process comprises the steps of:

(A) reacting the feedstock in the presence of a dehydrocyclodimerisation catalyst to produce a product comprising aromatic hydrocarbons, hydrogen and methane, (B) separating the product of step (A) into an aromatic hydrocarbon fraction, a methane-rich gaseous fraction and a hydrogen-rich gaseous fraction, (C) feeding all or part of the methane-rich gaseous fraction separated in step (B) to a synthesis gas production unit, thereby to produce synthesis gas, and (D) contacting the synthesis gas from step (C) together with all or part of the hydrogen-rich gaseous fraction separated in step (B), thereby increasing the hydrogen to carbon monoxide ratio of the synthesis gas, with a Fischer-Tropsch conversion catalyst to produce a hydrocarbon product.

Preferably additional methane-containing hydrocarbon gas is fed to the synthesis gas production unit in step (C).

Advantages associated with the process of the invention are that by-product off-gas streams from the DHCD process can be fully utilised, the methane-rich gaseous fraction being used as feedstock to the synthesis gas production unit and the hydrogen-rich gaseous fraction being used to increase the hydrogen to carbon monoxide ratio of the synthesis gas to a value appropriate for F-T conversion, thereby either completely eliminating or considerably reducing the size of the synthesis gas shift operation and considerably reducing any carbon dioxide removal requirement.

STEP (A)

In step (A) of the process of the invention there may be used any suitable dehydrocyclodimerisation catalyst, though a gallium loaded ZSM-5 type aluminosilicate zeolite is preferred. The feedstock to this step may be either ethane, propane, butane, or a mixture thereof, which may also contain one or more of methane, ethylene, propylene or a higher olefin. A particularly suitable feedstock is the LPG separated from natural gas, typically by cryogenic means, methane recovered therefrom being a suitable feedstock to step (C) of the process. Typical process conditions, catalysts, catalyst treatments and other information pertinent to the operation of step (A) of the process may be found in our patent publication GBAs Nos. 1499199; 1561590 and 1537780 and EPAs Nos. 50021; 119027; 119023; 147111; 162636; 186949 and 202000 and 0215579 (unpublished European application No. 86306340.0), the disclosures of which are incorporated by reference herein.

BRIEF DESCRIPTION OF PATENT PUBLICATIONS PERTINENT TO STEP (A)

EPA 147111 shows a process for producing aromatic hydrocarbons comprising bringing into contact at a temperature below 580° C. a mixed hydrocarbon feedstock containing at least 50% w/w of $C_3$ and/or $C_4$ hydrocarbons and from 10 to 50% w/w of ethane with a catalyst composition comprising an aluminosilicate in which the molar ratio of silica to alumina is at least 5:1.

The mixed feedstock contains $C_3$ and/or $C_4$ hydrocarbons, as the major reactant. Specific examples of the $C_3$ and $C_4$ hydrocarbons are propane, propylene, n-butane, isobutane, n-butenes and isobutene. Of these propane and the butanes are the most preferred. The hydrocarbon feedstock suitably contains more than 50%, preferably at least 70% by weight of the $C_3/C_4$ hydrocarbons.

The mixed feedstock which is converted to aromatic hydrocarbons or gasoline blending components suitably contains less than 45% w/w of ethane, preferably from 15–45% w/w of ethane.

Ethane may be added to the $C_3/C_4$ components from an external source or as a recycled product generated during the aromatisation of $C_3/C_4$ feedstock. This technique of recycling ethane is especially preferably in a continuous process which, after an initial induction period, generates sufficient ethane for a steady state to be achieved while removing excess ethane with the methane by-product.

EPA No. 0186949 concerns a process for producing aromatic hydrocarbons comprising bringing into contact in the vapour phase at a temperature from 500° C. to 750° C. a hydrocarbon feedstock containing at least 10% by weight of $C_2$ hydrocarbons with a catalyst composition comprising (i) an aluminosilicate loaded with gallium as a gallium compound and/or as gallium ions and having a silica to alumina molar ratio of at least 5:1, and (ii) a compound of a metal from Group VIIB or Group VIII of the Periodic Table at pages 448 and 449 of the Handbook of Chemistry and Physics, 44th Edition, Ed. Hodgman, C. D. et al and published by The Chemical Rubber Publishing Co., Ohio USA.

EPA No. 0050021 has to do with a process for producing aromatic hydrocarbons comprising bringing into contact at a temperature between 580° C. and 750° C. a hydrocarbon feedstock containing at least 70% by weight of $C_2$ hydrocarbons with a catalyst composition comprising an aluminosilicate having gallium deposited thereon and/or an aluminosilicate in which cations have been exchanged with gallium ions, said aluminosilicates containing silica to alumina in a molar ratio of at least 5:1. The amount of gallium present in the catalyst compositions may vary for instance between 0.05 and 10% by weight of the total aluminosilicate in the catalyst composition; and, the gallium exchanged/impregnated zeolites may be combined with a porous matrix, e.g., silica, alumina, or other inorganic compositions to improve the mechanical strength of the catalyst.

EPA No. 0215579 (unpublished EPA No. 86306340.0) provides a process for producing liquid products rich in aromatic hydrocarbons comprising bringing into contact in the vapour phase and in the absence of oxygen at a temperature from 500° C. to 750° C. a hydrocarbon feedstock containing a major proportion of $C_2$ hydrocarbons and at least 5% by weight of methane with a catalyst composition comprising an aluminosilicate having a silica to alumina molar ratio of at least 5:1 and being loaded with a gallium compound or gallium oxide. The amount of gallium present in the catalyst compositions may vary, for instance between 0.05 and 10% by weight of the total aluminosilicate in the catalyst composition; and, the gallium loaded zeolite may also be combined with a porous matrix to improve mechanical strength. The gallium in the catalyst may be present as gallium oxide and/or gallium ions if cations in the aluminosilicate support have been exchanged with gallium ions.

The $C_2$ hydrocarbon in the feedstock in EPAs Nos. 0186949, 0215579 and 0050021 may be ethane, ethylene or mixtures thereof. The feedstock may contain in addition other open chain hydrocarbons containing between 3 and 8 carbon atoms as coreactants or a diluent which is inert under the reaction conditions. Specific examples of such additional coreactants are propane, propylene, n-butane, isobutane, n-butenes and isobutene. In EPA No. 0186949 the hydrocarbon feedstock contains at least 10%, suitably at least 50%, preferably at least 70% by weight of $C_2$ hydrocarbons; in EPA No. 0050021 the feedstock preferably contains at least 80% by weight of $C_2$ hydrocarbons; and, in EPA No. 0215579 the mixed feed contains at least 5% by weight of methane, preferably from 10–50% by weight of methane and the hydrocarbon feedstock (excluding methane) preferably contains at least 70% by weight of $C_2$ hydrocarbons.

GBA No. 1561590 relates to a process for producing aromatic hydrocarbons comprising bringing into contact at an elevated temperature a $C_3$-$C_{12}$ hydrocarbon feedstock and a catalyst composition comprising an aluminosilicate having gallium deposited thereon and/or an aluminosilicate in which cations have been exchanged with gallium ions, said aluminosilicate containing silica to alumina in a molar ratio of between 20:1 and 70:1. The amount of gallium present in the catalyst compositions may vary for instance between 0.1 and 10%, preferably between 0.5 and 7% by weight of the total aluminosilicate in the catalyst composition. And, the invention of GB No. 1561590 also comprises a zeolite composition comprising an aluminosilicate having a molar ratio of silica to alumina of between 20:1 and 70:1 in which cations have been exchanged with gallium ions.

By $C_3$-$C_{12}$ feedstock meant here and throughout the specification of GBA No. 1561590 is a feedstock containing a single hydrocarbon component or mixtures of saturated and/or unsaturated $C_3$-$C_{12}$ hydrocarbons. The feedstock is suitably a $C_3$-$C_8$ hydrocarbon feedstock. $C_4$ feeds containing isobutane and/or isobutene in the feedstock are particularly useful.

The aluminosilicates in EPA No. 147111 have a silica to alumina molar ratio above 5:1, suitably from 20:1 to 150:1, and are suitably MFI type zeolites; the aluminosilicates loaded with gallium in EPA No. 0186949 are preferably zeolites of an MFI or MEL type structure; the aluminosilicates which have gallium compounds loaded thereon in EPA No. 0215579 are suitably of an MFI structure; and the aluminosilicates of EPAs Nos. 0186949, 0050021 and 0215579 suitably have a silica to alumina ratio between 20:1 and 150:1 (cf. "Chemical Nomenclature, and Formulation of Compositions, of Synthetic and Natural Zeolites," IUPAC yellow booklet, 1978, and zeolite structure types published by The Structure Commission of the International Aeolite Association entitled "Atlas of Zeolite Structure Types", by Meier, W. M. and Olsen, D. H. (1978), distributed by Polycrystal Book Service, Pittsburgh, Pa, USA).

The zeolites of EPAs Nos. 147111, 0215579, 0186949 and 0050021 may be selected from zeolites of the general formula $M_{2/n}O.Al_2O_3.ySiO_2.zH_2O$ wherein M is a cation which is a positively charged ion selected from a metal ion or an organic ion of valence n and a proton, y is an integer greater than 5 and z is from 0 to 40. The metal cation, M, is preferably an alkali metal or alkaline earth metal ion, or, as per EPA No. 147111 a proton, or as per EPAs Nos. 0186949, 0050021 and 0215579 preferably sodium or potassium ions. As per EPAs Nos. 0186949, 0050021 and 0215579, the organic cations may be represented by the formula $R^1R^2R^3R^4N^+$ or by an ion derived from the amine $R^1R^2R^3N$, the diamine $R^1R^2N(CH_2)_xNR^3R^4$ or pyrrolidine where $R^1R^2R^3$ and R[4] may be H, $CH_3$, $C_2H_5$, $C_3H_7$, $C_4H_9$ or $-CH_2CH_2OH$ and x equals 2, 3, 4, 5 or 6. A typical example of the MFI zeolite from EPAs Nos. 147111, 050021, 0215579 and 0186949 is ZSM-5 and EPAs Nos. 0186949, 0050021 and 0215579 provide that other zeolites of the ZSM variety, for example ZSM-8, ZSM-11, ZSM-12 and ZSM-35 may also be used. These are extensively described in a number of publications including U.S. Pat. No. 3,970,544 (Mobil). These zeolites are usually produced from a silica source, an alumina source, an alkali metal hydroxide and an organic nitrogen containing cation or a nitrogen containing base as template. The nitrogen-containing base may be organic such as an alkanolamine, for example diethanolamine, or inorganic, e.g. ammonia. Zeolites made in this manner are described in our published EPAs Nos. 0002899, 0002900 and 0030811. Zeolites derived by process of EPA No. 30811 are preferred in EPA No. 0186949.

The aluminosilicate employed in GBA No. 1561590 may be selected from zeolite-Beta and zeolites of the general formula: $M_{2/n}O.Al_2O_3.ySiO_2.zH_2O$ wherein M is a cation which is a positively charged ion selected from a metal ion, an organic ion and a proton of valence n, W is either aluminum or mixtures thereof with gallium, Y is silicon, y is an integer between 20 and 70 and z is from 0 to 40. The metal ion is preferably an alkali metal or alkaline earth metal ion, preferably sodium or potassium ions. The organic ions may suitably be represented by formulae as per the recitation regarding EPA No. 0186949, supra; and the ZSM variety of zeolites, for example ZSM-5, ZSM-8, ZSM-11, ZSM-12 and ZSM-35 are particularly preferred.

The aluminosilicates employed in EPA No. 147111 may be used for the hydrocarbon conversion in the as synthesised form and in the hydrogen form. It is however preferable to load the aluminosilicate with a catalytic component such as a metal compound or a metal ion. Compounds and ions of gallium are particularly preferred; and, the amount of gallium in the catalyst compositions may vary for instance between 0.05 and 10% by weight of the total aluminosilicate in the catalyst composition.

In order to produce a gallium loaded catalyst which has adequate life and activity the as synthesised zeolite is suitably subjected to a series of treatments. The series of treatments may include (a) washing the as synthesised zeolite with a dilute acid e.g. nitric acid;
(b) drying the washed, acid-treated zeolite from (a);
(c) calcining the dried zeolite from (b) at an elevated temperature, e.g. above 500° C.;
(d) loading the calcined zeolite with a gallium compound or gallium ions by well known impregnation or ion-exchange techniques; and
(e) binding the gallium loaded zeolite in a binder with a porous matrix such as e.g. silica or alumina.

Catalysts prepared in this manner have a high initial activity but this may decline rapidly because of an accompanying high rate of carbon deposition. However, it has been found that the catalyst can be partially deactivated so that the carbon deposition is significantly reduced with only a small effect on activity. This controlled deactivation may be produced by treating the catalyst with steam or by a high temperature dry calcination.

The steam treatment may be carried out with pure or diluted steam, preferably 10 to 40% vol/vol at temperatures over 400° C., preferably 500° to 650° C. The alternative dry temperature calcination may be carried out at temperatures above 600° C., preferably 700°-900° C. These treatments may, depending upon the method of zeolite preparation, allow the initial calcination step (c) to be eliminated but are normally carried out in addition to the initial calcination.

The as synthesised zeolite after washing, drying and calcination may be loaded with gallium either by exchanging cations in the zeolite and with gallium ions or by impregnating the zeolite with a gallium compound.

In EPAs Nos. 147111 and 0050021 and GBA No. 1561590 where the cations in the aluminosilicate can be exchanged for gallium ions, the gallium ion is suitably provided as an aqueous solution of a gallium salt such as for instance gallium nitrate, gallium chloride and gallium sulphate. Such catalysts may be prepared by conventional ion exchange techniques and the catalysts so produced are subsequently dried. For example an aqueous solution of a gallium compound such as gallium nitrate may be placed in contact with the aluminosilicate at ambient or elevated temperature, e.g. by refluxing. The exchanged aluminosilicate is then separated by decantation followed by filtration, washed several times with deionised water and finally dried. Before addition to the aqueous solution of the gallium compound, the aluminosilicate may be treated in the manner described in our published copending European Patent Application No. 0024930.

Alternatively, in the processes of EPAs Nos. 147111 and 0050021 and GBA No. 1561590, the gallium loaded zeolite may be produced by conventional impregnation techniques in which gallium or a gallium compound e.g. gallium oxide, is impregnated on the surface of the aluminosilicate or is incorporated in the intracrystalline zeolite cavities as such or as a gallium compound which gives rise to gallium oxide during activation of the catalyst prior to contact with the hydrocarbon feedstock. An example of a suitable gallium compound is gallium nitrate.

The impregnation may be achieved by preparing a solution, suitably an aqueous solution, of a gallium compound such as for example gallium nitrate and adding a conventional aluminosilicate to this aqueous solution with thorough stirring to form a paste. The paste is subsequently dried at an elevated temperature in vacuum.

Where the catalyst composition is prepared by using a compound of gallium which ionises in aqueous solution, for example gallium nitrate, some of the gallium ions may be exchanged with the cations in the aluminosilicate even if the preparation was by impregnation of the aluminosilicate.

The process of EPA No. 147111 is suitably a gas phase process and the conversion of the mixed feedstock to aromatics and/or aromatic containing gasoline blending components is suitably carried out at a temperature above 450° C., preferably from 475°-575° C. Reaction pressures used are suitably from 1-20 bar, preferably from 2-10 bar. The mixed feedstock is suitably brought into contact with the catalyst composition for a duration of 1-50 seconds, preferably from 5-20 seconds. The LHSV of the reactants is suitably from 0.5-8, preferably from 2-4.

In GBA No. 1561590, EPAs Nos. 0050021 and 0215579 the catalyst compositions are suitably activated prior to contact with hydrocarbon feedstock. The activation may be carried out by heating the catalyst at a temperature of in EPA No. 0050021 and GBA No.

1561590 between 400° and 650° C. and in EPA No. 0215579 between 400° and 750°, and, in GBA No. 1561590 and EPAs Nos. 0050021 and 0215579 preferably between 500° and 600° C. Activation may be carried out in an atmosphere of hydrogen, air or a gas inert under the reaction conditions such as nitrogen, but as per GBA No. 1561590, preferably in an atmosphere of hydrogen, as per EPA No. 0050021, preferably in an atmosphere containing oxygen, and, as per EPA No. 0215579 the gas may contain or consist of steam. The activation may be carried out in the reactor itself prior to the reaction. The catalyst composition is suitably used as a fixed bed. And, in EPAs Nos. 0050021 and 0215579 the catalyst composition may also be used in a fixed bed, a moving bed or a fluidised bed.

The hydrocarbon feedstock as hereinbefore described and described in GBA No. 1561590 is thereafter passed preferably in the vapour phase over the catalyst composition at a temperature between 450° and 700° C. preferably between 500° and 600° in an inert atmosphere. The inert atmosphere may be provided by a gas inert under the reaction conditions such as nitrogen. The products of the reaction are then identified and isolated.

The hydrocarbon feedstock as hereinbefore described and described in EPA No. 0050021 is thereafter contacted in the vapor phase with the catalyst composition at a temperature between 580° and 750° C. preferably between 580° and 650° C. in an inert atmosphere in the absence of oxygen. The inert atmosphere may be provided by a gas inert under the reaction conditions such as nitrogen distillation. Any unreacted ethane or ethylene recovered from the reaction products may be recycled to the aromatisation reaction.

The hydrocarbon feedstock as hereinbefore described and described in EPA No. 0215579 is thereafter contacted in the vapour phase with the catalyst composition at a temperature from 500° to 750° C. preferably from 580° to 650° C. in an inert atmosphere in the absence of oxygen. The inert atmosphere may be provided by a gas inert under the reaction conditions such as nitrogen. In fact, once the reactor has been initially flushed with an inert gas such as nitrogen to remove any oxygen or oxidising gases, there is no need to add further amounts of the inert gas to the reaction system. Any unreacted ethane or ethylene recovered from the reaction products may be recycled to the aromatisation reaction. The reaction is suitably carried out at a pressure from atmospheric to 30 bar, preferably from 3-20 bar. The WHSV of the feedstock with respect to the catalyst in the reaction is suitably from 0.1-10.

In EPA No. 0186949, the compound of a metal from Group VIIB or Group VIII of the Periodic Table may also be incorporated into the catalyst composition by impregnation or ion-exchange. Specifically, the Group VIIB and Group VIII metals are preferably selected from rhenium and iridium and these may be present in the catalyst compositions as the oxides or as the respective ions. These oxides or ions may be suitably provided from a solution e.g. aqueous solution, of the respective metal salt such as for instance rhenium trichloride, ammonium perrhenate or iridium tribromide. Alternatively the gallium loaded zeolite may be intimately mixed with a Group VIIB or Group VIII metal compound.

In EPA No. 0186949, the aluminosilicate may be loaded with the compounds of gallium and the Group VIIB or Group VIII metal in either order or a mixture of the two compounds may be used for simultaneous loading of the aluminosilicate. It is preferable to load the aluminosilicate with the Group VIIB or Group VIII metal compound prior to loading with gallium.

Whichever method of catalyst preparation is used, the amount of gallium present in the catalyst compositions of EPA No. 0186949 may vary for instance from 0.05 to 10% by weight of the total aluminosilicate in the catalyst composition. The gallium exchanged or impregnated zeolite thus obtained may be combined with a porous matrix, e.g. silica or alumina or other inorganic compositions to improve the mechanical strength of the catalyst.

The amount of Group VIIB or Group VIII metal present in the catalyst composition of EPA No. 0186949 is suitably from 0.05 to 10%, preferably from 0.1 to 0.8% w/w of the total composition.

The catalyst composition of EPA No. 0186949 may be activated as described above with reference to GBA No. 1561590. The catalyst composition of EPA No. 0186949 is suitably used in a fixed bed, a moving bed or a fluidised bed.

The hydrocarbon feedstock in EPA No. 0186949 is thereafter contacted in the vapour phase with the catalyst composition at a temperature from 500° to 750° C. preferably from 570° to 650° C. in an inert atmosphere in the absence of oxygen. The inert atmosphere may be provided by a gas inert under the reaction conditions such as nitrogen distillation. The reaction is suitably carried out at a WHSV for the reaction of 0.2 to 10, preferably from 0.5 to 2.0. The reaction pressure is suitably from 1-20 bar, preferably from 1-10 bar. Any unreacted $C_2$ hydrocarbon feedstock e.g. ethane or ethylene is recovered from the reaction products and may be recycled to the reaction along with the fresh hydrocarbon feedstock to be aromatised.

EPA No. 0162636 has to do with a process for the conversion of a mixed aliphatic hydrocarbon feedstock which is gaseous under ambient conditions into liquid products capable of being used as gasoline blending components said process comprising, (a) passing in an olefin reaction stage the mixed feedstock over a partially deactivated catalyst, (b) separating the reaction products from the olefin reaction stage into liquid and gaseous products, (c) passing in a paraffin reaction stage the separated gaseous products from the olefin reaction stage over a catalyst having an activity greater than that of the catalyst in the olefin reaction stage, and (d) separating and recovering the liquid products from the reaction products emerging from the paraffin reaction stage.

The mixed aliphatic hydrocarbon feedstock used as reactant comprises paraffins and olefins which are gaseous under ambient conditions. The mixed feedstock suitably contains at least 20%, preferably from 20-90% w/w of olefins. A typical mixed hydrocarbon feed is the $C_3$ and $C_4$ by-product stream from a fluid bed catalytic cracker which normally contains from 60-75% w/w of olefins. Such a typical feed may be mixed with a range of other refinery streams to achieve a wide variety of feed compositions.

The catalysts used for the paraffin and olefin reaction stages of the conversion reaction may be of the same or different type provided that the catalyst used in the olefin reaction stage has relatively lower activity than that used in the paraffin reaction stage. It is preferable to use the same type of catalyst and the difference in relative activities may be brought about by partial coking of the catalyst. The partial coking may, for instance, be achieved by passing an olefin or a paraffin stream over the catalyst at elevated temperature in order to deposit some carbon over the catalyst and thereby to partially deactivate the catalyst. Where coking or carbon deposition is used to partially deactivate the catalyst, the amount of carbon deposited on the catalyst is suitably from 3 to 20% w/w of the total catalyst. The deactivated catalyst so formed is then used as the olefin reaction stage catalyst and a freshly prepared or regenerated catalyst is used as the paraffin reaction stage catalyst.

In practice the mixed gas may be fed to an olefin reactor containing the partially deactivated catalyst, the paraffins in the gas acting as a heat sink to moderate the exothermic reaction of the olefins. The liquid is then separated from the product, in order to prevent degradation in the paraffin reactor, and the paraffinic gases, including some produced from the olefins in the olefin reaction stage, may then be fed to a paraffin reactor containing the newly regenerated catalyst. The liquid obtained from this paraffin reactor is separated and the mixed gas fed to a column where any residual paraffins e.g. propane and butane, are recovered for recycle. The recycle stream may return to either the paraffin reactor or to the olefin reactor, the latter being chosen if further moderation of the exothermic reaction is required.

The reaction conditions in the two reactors may vary over a moderately wide range. Typically, in the olefin reactor, the partially deactivated catalyst suitably contains 3-20% w/w of carbon deposited thereon and the reaction is carried out at a temperature from 200°-500° C., an LHSV of 1 to 101 and a pressure of 1-20 bar absolute. In the paraffin reactor, the catalyst is preferably a freshly produced or freshly regenerated catalyst. The reaction in this case is suitably carried out at a temperature from 400°-600° C., an LHSV of 0.5-8 and a pressure of 1-20 bar absolute.

The catalyst that may be used in the process of the invention of EPA No. 0162636 is preferably a gallium oxide loaded MFI-type zeolite although other catalysts known in the art as being capable of converting gaseous paraffins to liquid products may also be used. Where a gallium loaded MFI-zeolite is used the zeolite preferably contains from 0.1 to 10% of gallium based on the total catalyst. The gallium may be loaded onto the zeolite by well known ion-exchange or impregnation techniques. A typical example of such a process is that described above with reference to GBA No. 1561590. Instead, a gallosilicate of the type described in our EP No. 0106478 may be used as catalyst.

The typical advantages of the improved process of the invention of EPA No. 0162636 are that:
(a) the paraffinic components in a feed react only at temperatures above 450° C. but at these temperatures the olefinic components deposit carbon on the catalyst at a much faster rate than paraffins. Therefore the controlled two stage process diminishes problems of carbon deposition encountered by one stage processes using a single catalyst and one set of reaction conditions;
(b) the selectivity to liquid products from olefins is increased by using a lower temperature in the first stage because formation of methane and ethane is reduced; and
(c) the partially deactivated catalyst for olefin conversion further reduces formation of methane and ethane. Moreover the lower overall rate of carbon deposition also reduces the frequency of catalyst regeneration and the regenerative load on the system.

GBA No. 1499199 relates to a process for producing aromatic hydrocarbons comprising subjected a $C_4$ feedstock as hereinafter defined to dehydrocyclodimerisation substantially in the absence of oxygen and in the presence of a catalyst composition comprising an alumina promoted by zinc or a compound of zinc.

By $C_4$ feedstock is meant here and throughout the specification GBA No. 1499199 feedstock containing a single $C_4$ component or mixtures of saturated and/or unsaturated $C_4$ hydrocarbons. Although the presence of isobutene in the feedstock would be preferable, it is not an essential component.

In the catalyst composition of GBA No. 1499199 zinc may be present as such or in the form of a compound. Preferred examples of zinc compounds are zinc oxide and zinc sulphate. The amount of zinc present in such catalyst compositions may vary between 0.1% and 10%, preferably between 2.5% and 7% by weight of the total alumina in the catalyst composition. The alumina used in the catalyst composition may be any of the conventional types such as eta-alumina, gamma-alumina or boehmite, eta-alumina and boehmite being most preferred.

The catalyst composition of GBA No. 1499199 is prepared by impregnating the alumina with an aqueous solution of a soluble zinc compound, e.g. zinc nitrate. The paste so formed may be evaporated to dryness under vacuum and then pyrolysed at elevated temperature in a stream of air.

GBA No. 1537780 shows a process for producing aromatic hydrocarbons comprising contacting at an elevated temperature a $C_3-C_8$ aliphatic hydrocarbon feedstock with a catalyst composition comprising gallium on a silica support wherein the silica has a surface area of over 500 meter$^2$/gram and a pore volume of less than 0.8 ml/gram. By $C_3-C_8$ feedstock is meant here and throughout the specification of GBA No. 1537780 a feedstock as per the recitation regarding GBA No. 1561590, supra.

The silica support of GBA No. 1537780 has a surface area of over 500 meter$^2$/gram, preferably between 600 and 800 meter$^2$/gram. The pore volume of the silica support is preferably between 0.5 ml/gram and 0.05 ml/gram. It is also preferable that the mean pore diameter of the silicas in less than 65A. The higher surface area and low pore volume can result in the use of a lesser amount of gallium than hitherto and it has also been found surprisingly that the smaller amount of gallium is more active. The silica supports suitably have surface hydroxyl groups available for exchange.

The gallium in the catalyst composition may be present as gallium oxide and/or gallium ion depending upon whether the silica support has free hydroxyl groups available on the surface thereof for exchange.

If the silica support is free from surface hydroxyl groups, the gallium may be impregnated on the surface thereof as gallium oxide or as a gallium compound which gives rise to gallium oxide during activation of the catalyst prior to contact with the hydrocarbon feedstock. Examples of such gallium compounds include gallium nitrate, gallium sulphate and gallium chloride. Conventional impregnation techniques may be used to produce there catalysts.

If the silica support has surface hydroxyl groups available for exchange, gallium ions may be exchanged for the hydrogen in such surface hydroxyl groups on the silica support. The gallium ion may be provided by aqueous solutions of gallium salts such as for instance gallium nitrate, gallium chloride or gallium sulphate. Such catalysts may be produced by conventional ion exchange techniques and the catalysts so produced are subsequently dried.

Whichever method is used, the amount of gallium present in such catalyst compositions may vary for instance between 0.1 and 10%, preferably between 0.5 and 5% by weight of the total support in the catalyst composition. The catalyst composition of the invention of GBA No. 1537780 may also contain other metals such as palladium, indium, germanium, chromium, tin and/or zinc in small quantities to improve the activity thereof.

The catalyst compositions of the processes of GBAs Nos. 1537780 and 1499199, as per GBA No. 15337780, may be activated prior to contact with the hydrocarbon feedstock by passing air, hydrogen or a gas inert under the reaction conditions such as nitrogen over the catalyst at or near the proposed reaction temperature preferably between 500° and 600° C. In GBA No. 1499199 the prepared catalyst may be formed as a fixed bed, in GBA No. 15337780 it is suitably used as such and in both said GBAs, the activation may be carried out in the reactor tube itself.

After activation, the feedstock (hydrocarbon in GBA No. 1537780, $C_4$ in GBA No. 1499199) is thereafter passed over the respective catalyst at an elevated temperature for instance between 450° and 700° C., preferably between 500° and 600° C. in an atmosphere which is inert under the reaction conditions, such as nitrogen. In GBA No. 1499199 pressure of up to 20 atmosphere may be used for the reaction. The products of the respective reaction are then isolated and identified.

EPA No. 119027 provides a process for activating an alminosilicate zeolite loaded with a gallium compound as catalyst said process comprising bringing into contact the zeolite, before or after loading thereof with gallium, with steam and concurrently or separately with hydrogen, both stages being carried out at an elevated temperature. The activated loaded zeolite may be used as a catalyst for converting $C_4$ or $C_3$ and $C_4$ to aromatics, e.g., by placing it in a reactor, heated at 500° or 550° C., passing air over the catalyst for 4 or 2 hours, purging with nitrogen, and feeding butane over the catalyst (550° C., atmospheric pressure, 1.6–1.7 seconds, or 2 LHSV, 535° C.).

EPA No. 119023 concerns a process for activating an aluminosilicate loaded with a compound of a metal from Group IIIb of the Periodic Table said process comprising bringing into contact the unloaded zeolite with steam at an elevated temperature prior to loading thereof with a compound of a metal from Group IIIb of the Periodic Table. The activated loaded zeolite may be used as a catalyst for converting n-$C_4$ to aromatics, e.g., by placing it in a reactor, heated at 550° C. and maintained at that temperature for 4 hours in dry flowing air; flushing with nitrogen, and then bringing n-butane into contact with the catalyst (1 bar absolute pressure, 5 WHSV, catalyst bed temperature 535° C. by external heating).

Specific examples of the Group IIIb metals which may be used as their compounds to load the zeolites in the present invention include aluminum, gallium, indium and thallium. Compounds of gallium, especially the oxide are the most preferred. Loading methods are well known to those skilled in the art. Examples of such methods are ion exchange and impregnation of the zeolite with aqueous solutions of the relevant compound or ion.

The expression "activating an aluminosilicate zeolite" as used herein and throughout EPAs Nos. 119023 and 119027 means activating unused, freshly prepared zeolites and restoring the activity of zeolites which the partially or wholly activated during hydrocarbon conversion.

The zeolites which may be activated by the processes of EPAs Nos. 119023 and 119027 are aluminosilicates which preferably have a high silica to alumina ratio, i.e. greater than 5:1. Methods of preparing such zeolites are described for instance in our published European Patent Application Nos. 0024930 and 0030811. Particularly useful zeolites are MFI-type zeolites.

The activation process of EPA No. 119027 is particularly effective on zeolites which are low in their content of sodium or other alkali metal ions.

In EPA No. 119027 the steam treatment may be carried out on the zeolite whether or not it has been loaded with a catalytically active component such as e.g. gallium oxide. Moreover, the steam treatment may be carried out as part of a regeneration procedure on a catalyst which has been partially or wholly deactivated in use.

In EPA No. 119023 the steam treatment can be carried out at any stage in the preparation of an active catalyst provided it precedes the loading step with a catalytically active Group IIIb metal compound such as e.g. gallium oxide. Thus for example, if the liquor-free zeolite contains an organic (nitrogenous) base which requires removal by calcination in air (for example in order to improve catalytic performance), the steaming step can be conveniently included in this calcination. Alternatively the steaming step can be effected after this calcination. The steaming step can be carried out before or after binding. The steaming step is preferably carried out on a zeolite in which substantially all of the exchangeable metal ions such as sodium ions have been exchanged with hydrogen or ammonium ions.

The various embodiments of the process of EPA No. 119027 showing the sequence in which the steps of calcination (C), steaming (S), loading (G) with an active catalyst component, and binding (B) may be carried out on the zeolite can be notationally summarised as follows:

1. C (s)* G B
2. C (s)* B G
3. C S G B
4. C S B G
5. C G S B
6. C G B S
7. C B G S
8. C B S G
9. B C (s)* G
10. B C S G
11. B C G S

* C (s)—represents simultaneous calcination and steaming. Of these, sequences 1, 3, 6, 9, 10 and 11 are particularly preferred.

In both EPAs Nos. 119023 and 119027 the steam treatment of the zeolite is suitably carried out using steam as such or a carrier gas stream comprising steam. The carrier gas stream may be a gas inert under the reaction conditions e.g. nitrogen, or air. The gas stream used for steam treatment suitably contains between 1 and 100% by volume of steam, preferably between 10 and 100% by volume of steam. The steam treatment is suitably carried out at 0.01–1.0 MPa, preferably at 0.1 MPa.

In both EPAs Nos. 119023 and 119027 the steam treatment is suitably carried out at a pressure of between 0.01 and 1.0 MPa, preferably at 0.1 MPa and a temperature between 300° and 750° C., preferably between 500° and 700° C. for a duration of between 5 minutes and 200 hours, preferably between 1 and 12 hours. Increasing the severity of one or more parameters may allow reduction of the severity of one or more parameters. For instance, raising the steaming temperature can be expected to shorten the duration of steaming needed.

The steam treatment referred to herein and in EPA No. 119023 may be preceded or followed by any conventional oxidation and reduction treatments. That is, the zeolite may for instance be treated with air and/or hydrogen at an elevated temperature in either order after the steam treatment step or the metal loading step.

The steam treatment referred to herein and in EPA No. 119027 may be preceded by, concurrent with or followed by the hydrogen treatment. The hydrogen treatment step is preferably carried out after the zeolite has been loaded with the gallium compound. That is, the gallium loaded zeolite may for instance be treated with air and/or hydrogen in either order at an elevated temperature prior to, during or after the steam treatment step. However, the steam treatment step may precede the gallium loading step in which case it is preferred that the hydrogen treatment follows steam treatment and gallium loading.

The hydrogen treatment is suitably carried out in a gaseous stream containing between 1 and 100% volume of hydrogen, preferably between 30 and 100% v/v hydrogen. The hydrogen treatment may be carried out at 450° to 700° C., preferably 525°–650° C. for 5 minutes to 200 hours, preferably for 1 to 20 hours and a pressure of 0.01 to 1.0 MPa, preferably at 0.1 MPa. Increasing the severity of one or more parameters may allow reduction of the severity of one of the other parameters. For instance, raising the temperature of hydrogen treatment may reduce the duration of this treatment needed.

The steam and hydrogen treated gallium-loaded zeolite catalyst may, if desired, have a final treatment in an oxidising atmosphere such as e.g. air, at elevated temperature. The steam and hydrogen treatments may be carried out on a gallium loaded zeolite, which has been wholly or partially deactivated in use as a hydrocarbon conversion catalyst, a part of a regeneration procedure to restore and improve the activity thereof. The steam or hydrogen treatment of the zeolite may be preceded or followed by one or more conventional oxidation, calcination or reduction steps.

EPA No. 0202000 concerns a process for the conversion of $C_2$–$C_6$ paraffinic hydrocarbons to aromatic hydrocarbons over a gallium loaded zeolite at elevated temperature characterised in that the process comprises the steps of:

(a) bringing a feedstock comprising predominantly ethane into contact with a freshly prepared or regenerated gallium loaded zeolite catalyst at a temperature from 550° to 650° C. over a period from 10 to 50 hours;

(b) bringing a paraffinic feedstock comprising predominantly $C_3$–$C_6$ hydrocarbons into contact with the residual catalyst from step (a) after contact with ethane at a temperature from 470° to 580° C. over a period from 40 to 200 hours;

(c) regenerating the residual catalyst from step (b) after contact with the $C_3$–$C_6$ hydrocarbons; and (d) recycling the regenerated catalyst from step (c) to step (a).

The $C_3$–$C_6$ paraffinic hydrocarbon feedstock is preferably propane or a butane. Steps (a) and (b) are both suitably carried out at a pressure in the range of 1 to 20 bar absolute using a WHSV of 0.3 to 8. The gallium loaded zeolite suitably contains from 0.1 to 10% by weight of gallium, preferably from 0.2 to 5% by weight of gallium. The zeolite is an aluminosilicate which preferably has a high silica to alumina ratio, i.e. greater than 5:1. Methods of preparing such zeolites are claimed and described in our EPAs Nos. 0024930 and 0030811. Zeolites of the MFI type are most preferred. The gallium can be loaded on the zeolite from a gallium compound by ion-exchange or impregnation by well known techniques of the art, e.g. as described in EPA No. 0050021. The gallium loaded zeolite may be activated prior to reaction with ethane using the process described for instance in EPA No. 0119027.

The sequential reaction of EPA No. 0202000 is suitably carried out in a pressure swing reactor system. Alternatively a moving bed system may be used whereby fresh catalyst is fed to the first reactor and it gradually deactivates due to deposition of carbon as it passes through a series of reactors, ethane is fed to the first reactor and the $C_3$–$C_6$ hydrocarbons to any of the subsequent reactors.

Upon reaction with ethane in step (a), the gallium loaded catalyst is deactivated to some extent. This is due to the deposition of carbon in a concentration of e.g. 3 to 10% w/w on the catalyst in step (a). However, in spite of the deactivation of the original catalyst in step (a), the residual catalyst surprisingly retains sufficient activity to allow conversions of the higher $C_3$–$C_6$ paraffin hydrocarbons into aromatics at relatively lower temperatures in step (b). Moreover, in step (b) the selectivities to liquid hydrocarbons are substantially the same as those observed with a fresh catalyst. The catalyst deactivated in step (b) may be regenerated using conventional method, e.g. by burning off the deactivating carbon deposited thereon using air diluted with an inert gas e.g. nitrogen at elevated temperature.

STEP (B)

The products to step (A) are aromatic hydrocarbons comprising a mixture of benzene, toluene and xylene (BTX), methane and hydrogen. In step (B) these products are separated into BTX, a methane-rich gaseous fraction and a hydrogen-rich gaseous fraction. This separation may be effected in conventional manner.

STEP (C)

In step (C) all or part, preferably all, the methane-rich gaseous fraction separated in step (B) is fed, preferably together with additional methane-containing hydrocarbon gas, to a synthesis gas production unit. Suitably the methane-containing hydrocarbon gas may be any gas principally comprising methane, for example natural gas and/or the methane recovered from and LPG separation unit. It is preferred to use the methane separated from natural gas to provide LPG feedstock for step (A) of the process. The synthesis gas production unit may suitably be a steam reforming unit, an autothermal reforming unit or a partial oxidation unit, or a combination of primary steam reforming and secondary autothermal reforming, as described for example in our copending UK application publication No. 2179366. Preferably the synthesis gas production unit is a partial oxidation unit because in contrast to steam reforming and/or autothermal reforming routes partial oxidation processes for the production of synthesis gas generally can not produce a synthesis gas having a hydrogen to carbon monoxide ratio greater than 2:1. The oxidative synthesis gas production unit may be either a catalysed or an uncatalysed partial oxidation unit, both of which are conventional in the art. A particularly suitable synthesis gas production unit is a catalytic partial oxidation unit which may take the form of a fluidised bed or a spouted bed of reforming catalyst to which is fed under appropriate conditions of temperature and pressure the aforesaid methane-containing feedstock, steam and an oxygen-containing gas, in suitable proportions. Suitably the oxygen-containing gas may be molecular oxygen, which may be diluted with an inert gas, for example nitrogen, suitably in proportions appreciably less than those pertaining in air. Preferred synthesis gas production units and methods for operating them are described in our copending European application publication Nos. 163385, 164864 and 178853, the contents of which are incorporated by reference herein.

BRIEF DESCRIPTION OF PATENT PUBLICATIONS PERTINENT TO STEP (C)

EPA No. 163385 provides a process for the production of synthesis gas and higher hydrocarbons in which (a) a saturated hydrocarbon and an oxygen containing gas having a ratio of hydrocarbon to oxygen of greater than the stoichiometric ratio for complete combustion are introduced into a bed of an inert particulate material, (b) the upward flow rate of the hydrocarbon/oxygen containing gas stream being sufficiently large to fluidise or to produce a spouting action of the bed material, whereby at least a part of the particulate material is thrown up above the bed surface and subsequently falls back into the bed, (c) the hydrocarbon and oxygen containing gas being ignited and reacted together and (d) the products of the reaction being withdrawn.

EPA No. 178853 provides a process for the production of synthesis gas and hydrocarbons in which (a) a saturated hydrocarbon and an oxygen containing gas having a ratio of hydrocarbon to oxygen of greater than the stoichiometric ratio for complete combustion are introduced together with hydrogen into a bed of particulate material (b) the upward flow rate of the gases being sufficiently large to fluidise or to cause a spouting action of the bed material (c) the hydrocarbon, oxygen containing gas and hydrogen being ignited and reacted together and (d) the products of the reaction being withdrawn.

EPA No. 0164864 provides a process for the production of synthesis gas in which (a) a saturated hydrocarbon and an oxygen containing gas having a ratio of hydrocarbon to oxygen of greater than the stoichiometric ratio for complete combustion are introduced into a bed of particulate material, the bed comprising material which is catalytically active for partial oxidation and/or steam reforming reactions, (b) the upward flow rate of the hydrocarbon/oxygen containing gas stream being sufficiently large to cause a spouting action of the bed material, (c) the hydrocarbon and oxygen reacting together and (d) the products of the reaction being withdrawn.

In both EPAs Nos. 163385 and 178853 the preferred composition of the respective saturated hydrocarbon/oxygen containing or hydrogen, saturated hydrocarbon/oxygen containing gas mixture is pressure dependent. At atmospheric pressure, the preferred composition in EPA No. 163385 or as in EPA No. 176685 hydrocarbon/oxygen molar ratio is 1.1 to 5 times the stoichiometric ratio of hydrcarbon/oxygen for complete combustion to carbon dioxide and water. The preferred molar ratio of $H_2$ to $O_2$ is 5 or less. These limits are extendible if operation at system pressures of greater than atmospheric are envisaged or if the feed gases are pre-heated.

In EPA No. 0164864, the composition of the hydrocarbon/oxygen containing gas will depend upon the nature of the hydrocarbon. The ideal stoichiometry is:

$$C_nH_{2n+2} + n/2\ O_2 = nCO + (n+1)\ H_2$$

The preferred ratio of oxygen to hydrocarbon will be some value higher than ideal to satisfy the heat requirements of the reaction and to prevent Boudouard carbon formation:

$$CO_2 + C = 2CO$$

Using a methane feed typically the preferred methane/oxygen molar ratio will be in the range 1.6–1.9.

In EPAs Nos. 163385, 178853 and 0164864, commercial reactor systems would probably be operated at pressures above atmospheric and up to 50 bar or even higher.

In EPAs Nos. 163385, 178853 and 0164864 the reaction may be initiated in a number of ways. For example, the particulate material may be pre-heated by igniting and burning a near stoichiometric mixture, e.g., fuel and oxygen containing gas, in the bed until the bed temperature is great enough to sustain in reaction of the hydrogen and excess stoichiometric hydrocarbon/oxygen mixtures or the combustion of excess stoichiometric hydrocarbon/oxygen mixtures or the partial oxidation reaction. A typical steady state bed temperature, as per EPAs Nos. 163385 and 178853 is of the order 500°–1500° C., and is of the order of 800°–1200° C. without external heating, as per EPA No. 0164864.

In both EPAs No. 178853 and EPA No. 163385, the particulate bed material may be an inert temperature resistant refractory material which may include firebrick, quartz, carborundum, zirconia, silicon carbide, ceramics and certain forms of carbon, e.g., high density coke may be used. The shape of the particle bed material may be, for example, spherical, cylindrical, or amorphous. The particle size may vary from 0.01 to 10 mm in diameter, depending upon the particle density, the diameter of the reactor and feed inlet, and the feed gas flow rate. The particle size distribution for spouted bed operation is preferably as uniform a possible. In EPA No. 178853 particulate material having catalytic properties such as alumina may also be used.

The particulate material of the bed of EPA No. 0164864 comprises material which is catalytically active for partial oxidation and/or steam reforming reactions. Suitable catalytically active materials include a metal or metals of Group VIII of the Periodic Table of the Elements deposited on a porous refractory support. Nickel and iron are known catalytically active materials which may be used in the process of the invention. Mixtures of Group VIII metals, optionally containing alkali metal, may also be employed. Porous, particulate, freeflowing catalyst support materials suitable for use in the particulate bed include silica, alumina, silica-alumina, zirconia, titania, hafnia, silicon carbide, boron phosphate, diatomaceous earth and pumice. The bed may be diluted with inert temperature resistant refractory materials such as firebrick, quartz, ceramics. The shape of the particulate bed material may be, for example, spherical, or amorphous. The particle size may vary from 0.01 to 10 mm in diameter dependent upon the particle density, the diameter of the reactor and feed inlet and the feed gas flow rate. The particle size distribution is preferably as uniform as possible.

In EPAs Nos. 0164864, 178853 and 163385, the reactor vessel may be shaped so as to encourage recirculation of the bed particles in a vertical direction, e.g., an elongated column having a conical base portion wherein the base of the column is adapted to receive a nozzle for the introduction of reactants (the base portion contains the particulate material), the nozzle in connectable to a supply of feed gas(es), and a line enables products to be withdrawn.

For a single inlet feed nozzle, the preferred shape of the base portion is conical; the cone angle from the vertical is preferably from 10° to 40°. For the conversion of large quantities an array of reactors may be used, e.g., a plurality of integral units comprising a single compartmentalised bed or a multispouted bed. It is also possible to introduce further gas feeds to the bed through (a) further nozzle(s) which may direct the further feed in a counter current, parallel perpendicular or other direction relative to the spouting gas feed direction. And, carbon dioxide or water or steam may be introduced to the bed with the feed gases or through a separate injection point to control the reaction (e.g., quench) or reduce carbon formation.

DISCUSSION OF STEP (C) OF PRESENT INVENTION CONTINUED

The synthesis gas produced in step (C) will generally contain, in addition to hydrygen and carbon monoxide, carbon dioxide either originating from the feedstock and/or formed in the synthesis gas production step, and possibly also steam. In an optional step (C') this carbon dioxide and water are removed in conventional manner, for example by solvent absorption, together with steam.

STEP D

In step (D) the synthesis gas separated in step (C) is admixed with all or part of the hydrogen-rich gaseous fraction separated in step (B) for the purpose of increasing the hydrogen to carbon monoxide ratio thereof and contacted with an F-T conversion catalyst to produce a hydrocarbon product. The amount of hydrogen-rich gaseous fraction admixed is suitably sufficient to produce a hydrogen to carbon monoxide molar ratio greater than 2:1, preferably in the range from 2.05 to 2.2:1. In order to achieve this preferred range it may be necessary to either operate a hydrogen bleed or feed additional hydrogen, though in a preferred embodiment the total throughputs are adjusted to a value consistent with using the hydrogen-rich gaseous fraction without any adjustment of the hydrogen content thereof.

Suitable Fischer-Tropsch catalysts comprise one or more of the metals iron, cobalt or ruthenium, optionally supported on a suitable support, for example silica, alumina, titania or ceria. Suitably the catalyst may incorporate a crystalline zeolite, for example ZSM-5 or ultrastable zeolite Y. A preferred Fischer-Tropsch catalyst is one capable of converting synthesis gas to a mixture of gaseous $C_2$ to $C_4$ olefinic hydrocarbons and liquid $C_5+$ hydrocarbons. A particularly preferred catalyst is a ruthenium/ceria catalyst as described in our copending European applications publication Nos. 0169743, 0211577 and 0232962, the disclosures of which are incorporated herein by reference. In an alternative embodiment, a preferred Fischer-Tropsch catalyst is one capable of converting synthesis gas to waxy hydrocarbons, which hydrocarbons are convertible to liquid $C_5+$ hydrocarbons by contact with a zeolite under appropriate conditions. A preferred catalyst of this type is cobalt, suitably in combination with a support, for example zinc oxide, as described in our copending European application No. 87308211.9, the disclosure of which is incorporated herein by reference.

BRIEF DESCRIPTION OF PATENT PUBLICATIONS PERTINENT TO STEP (D)

The inventions of EPAs Nos. 0169743, 0232962 and 0211577 provide processes for the production of compositions for use after reductive activation as a catalyst in the conversion of synthesis gas to hydrcarbons of carbon number greater than one, which compositions in EPAs Nos. 0169743 and 0232962 have the formlua:

$$Ru_aA_bCeO_x \qquad (I)$$

and in EPA No. 0211577 has the formula:

$$Ru_aA_bXO_x \qquad (I)_1$$

wherein
A is an alkali metal,
X is a rare earth metal having atomic numbers from 57 to 71 inclusive,
x is a number such that the valence requirements of the other elements for oxygen is satisfied,
a in EPA No. 0169743 is greater than zero and less than 1% w/w, and in EPAs Nos. 0232962 and 0211577 is greater than zero and less than 5% w/w, based on the total weight of the composition, and
b is in the range from zero to 10% w/w, based on the total weight of the composition, and
Ce and O in EPAs Nos. 0232962 and 0169743 constitute the remainder of the composition, and in EPA No. 0211577, subject to the requirements of x,
X constitutes the remainder of the composition
which process in EPA No. 0169743 comprises the steps of:
(A) bringing together in solution soluble salts of the metals ruthenium and cerium and a precipitant and/or a hydroxide of an alkali metal or ammonium under conditions whereby there is formed a precipitate comprising ruthenium and cerium in the form of compounds thermally decomposable to their oxides, and
(B) recovering the precipitate obtained in step (A),
in EPA No. 0232962 the process comprises the steps of:
(A) adding a solution or solutions of soluble compounds of the metals ruthenium and cerium, and optionally also an alkali metal compound, to a solution of a precipitant comprising a carbonate and/or a bicarbonate and/or a hydroxide of an alkali metal or ammonium under conditions whereby there is formed a preciptate comprising ruthenium and cerium, and optionally also an alkali metal, in the form of compounds thermally decomposable to the metals and/or their oxides, and (B) recovering the precipitate obtained in step (A), and in EPA No. 0211577 the process comprises:

(A) bringing together at a temperature below 50° C. a rare earth metal oxide, a solution of a soluble salt of ruthenium and a precipitant comprising a carbonate and/or a bicarbonate and/or a hydroxide of an alkali metal or ammonium under conditions whereby ruthenium is precipitated in the form of a heat decomposable compound, (B) recovering the mixtured of a rare earth metal oxide and the precipitated ruthenium compound obtained in step A, (C) thermally decomposing thermally decomposable compounds comprised in the mixture recovered in step (B).

Preferably a in the formula (I) in EPA No. 0232962 is less than 1% w/w.

It has been found that catalysts differing from catalysts of the invention of EPA No. 0169743 in the respect that their ruthenium content is greater than 1% w/w tend to produce large quantities of methane, the actual proportion of methane increasing with increasing ruthenium content, whereas catalysts according to the invention of EPA No. 0169743 in which the ruthenium content is less than 1% w/w, preferably less than 0.5% w/w, are at the same time both active and selective to hydrocarbons other than methane, and in particular to aliphatic hydrocarbons of carbon number greater than 2, of which $C_5+$ hydrocarbons form a major proportion. Moreover the selectivity to unwanted carbon dioxide can be maintained within acceptable limits, unlike catalysts containing higher ruthenium loadings.

In formulae (I) and (I)$_1$ of the catalysts of EPAs Nos. 0169743, 232962 and 0211577 A is an alkali metal, which is preferably potassium as per EPAs Nos. 0169743 and 0232962 and sodium and potassium as per EPA No. 0211577. As per EPAs Nos. 0169743 and 232962, the amount b of alkali metal is preferably greater than zero and up to 5% w/w, even more preferably up to 2% w/w; and, as per EPA No. 0211577 the amount of b is less than 2% w/w, preferably less than 1% w/w and X is preferably cerium with ceria ($CeO_2$) a preferred rare metal oxide.

As regards step (A) of the process of EPA No. 0232962, a solution or solutions of soluble compounds of the metals ruthenium and cerium, and optionally also an alkali metal, is added to a solution of a precipitant comprising a carbonate and/or a bicarbonate and/or a hydroxide of an alkali metal or ammonium under conditions whereby there is formed a precipitate comprising ruthenium and cerium, and optionally also an alkali metal, in the form of compounds thermally decomposable to the metals and/or their oxides. Suitably the solution or solutions employed may be aqueous solutions. The compounds of ruthenium and cerium, and optionally also the alkali metal compound, may be contained in separate solutions and added to the precipitant solution in any order or they may be contained in a single solution and thereby added together to the precipitant.

In a preferred embodiment of the process of EPA No. 0232962 step (A) may be operated continuously by feeding simultaneously to a precipitate zone and mixing therein a solution or solutions of soluble compounds of the metals ruthenium and cerium, and optionally also an alkali metal, and a solution of the precipitant under conditions whereby there is formed a precipitate comprising ruthenium and cerium, and optionally also an alkali metal, in the form of compounds thermally decomposable to their oxides. The precipitation zone may suitably take the form of a vessel provided with means for separately introducing a solution of soluble compounds of ruthenium and cerium, and optionally also alkali metal, and a solution of the precipitant, the means for separately introducing the solutions being so arranged as to achieve mixing of the solutions, agitation means, pH measuring means and means for continuously withdrawing the suspended precipitate, for example an overflow pipe.

As regards step (A) of the process of EPA No. 0211577, the rare earth metal oxide may suitably be brought together with an aqueous solution of a water soluble salt of ruthenium, in which solution the rare earth metal oxide is substantially insoluble. Suitably an aqueous solution of the precipitant may be added to an aqueous solution of the ruthenium salt containing also the rare earth metal oxide, though other variants of the order of addition will be readily apparent to those skilled in the art and may be used if desired.

As regards step (A) of the process of EPA No. 0169743 the salts of ruthenium and cerium may suitably be brought together in aqueous solution. Suitably an aqueous solution of the precipitant may be added to an aqueous solution of water soluble salts of the metals, though other variations in the order of addition will be readily apparent to those skilled in the art and may be used if desired. With regard to EPAs Nos. 0211577, 0169743 and 0232962, any soluble salt of ruthenium may be employed, and it is convenient to use ruthenium in the form of the chloride because this is a commercially available form and, as per EPAs Nos. 0169743 and 0232962, any soluble salt of cerium may be used and it is convenient to use cerium in the form of the nitrate, for example cerrous nitrate. Commercially available cerrous nitrate, which contains rare earth metals other than cerium, may be employed if desired.

The precipitant in step (A) of EPAs Nos. 0211577, 0232962 and 0169743 is a carbonate and/or a bicarbonate and/or a hydroxide of an alkali metal preferably sodium or potassium as per EPA No. 0211577. Instead of using a pre-formed carbonate or bicarbonate it is possible to use the precursors of these salts, for example a water soluble salt and carbon dioxide. Alternatively, as per EPAs Nos. 023962 and 0169743, urea, which is thermally decomposable to carbon dioxide and ammonia, may be used. In any event, b in the aforesaid formulae (I) and (I)$_1$ of EPAs Nos. 0232962, 0169743 and 211577 will have a value greater than zero, which value may be adjusted if desired by washing or addition of further alkali metal compound. Alternatively, ammonium carbonate and/or bicarbonate and/or hydroxide may be employed as the precipitant, in which case the value of b in the catalyst as initially produced will be zero, though this value may subsequently be adjusted if desired by addition of alkali metal. In EPA No. 0232962, perferably ammonium bicarbonate, optionally mixed with an alkali metal bicarbonate, for example potassium bicarbonate, is used as the precipitant.

Further, with respect to EPAs Nos. 0232962 and 0169743, suitably the soluble salts of the metals ruthenium and cerium may be brought together at a temperature in the range from 0° to 100° C. In one preferred embodiment of both of said EPAs the temperature is suitably in the range from 60° to 100° C., preferably from 80° to 100° C. In another preferred embodiment of both of said EPAs the temperature is suitably below 50°

C., preferably below 30° C., for example ambient temperature. In EPA 0211577, the precipitation is preferably carried out at a temperature below 30° C., conveniently at room temperature, for example 15° to 25° C. as catalysts produced at low temperatures are generally more active than similar catalysts wherein the ruthenium is precipitated at high, for example, 80°-90° C., temperatures.

In EPAs Nos. 0169743 and 0211577, addition of the precipitant of the solution of metal salts causes the initially lwo pH of the mixture to rise. It is desirable in the preparation of catalysts according thereto that the final pH of the mixture is greater than 6, preferably in the range from 6 to 10, even more preferably in the range from 8 to 10. The precipitant may be added until a pH in the aforesaid range is achieved, whereupon the addition of further precipitant may be discontinued, thereby arresting the rise in the pH. After precipitation, it is preferred to maintain the mixture at a temperature close to boiling for a period of at least 15 minutes, preferably whilst stirring, for the purpose of completing the precipitation.

In EPA No. 0232962, precipitation may suitably be effected at a pH greater than about 6, preferably in the range from 6 to 10. Preferably the pH is substantially constant within the aforesaid range throughout the precipitation step. A substantially constant pH may suitably be achieved by using a large excess of the precipitant, for example about seven times the theoretical stoichiometric amount required for complete precipitation. Alternatively, a suitable buffer may be employed.

In continuous operation of step (A) of EPA No. 0232962 the solutions are preferably fed at a relative rate such as to achieve a substantially constant pH within the aforesaid ranges. In order to achieve a substantially constant pH it may be desirable to further feed a solution of an inorganic base, for example aqueous ammonia.

In order to improve the homogeneity of the catalysts in EPAs Nos. 0211577, 0232962 and 0169743, it is preferred to agitate the mixture during precipitation, suitably by mechinical stirring.

In both EPAs Nos. 0169743 and 0232962, the amounts of the ruthenium and cerium compounds and precipitant employed should be such as to satisfy the stoichiometric relationships in the formulua (I) and in EPA No. 0211577 the amounts of reagents employed should be such as to satisfy the stoichiometric relationships in formula (I)$_1$. Alternatively, as per EPAs Nos. 0169743 and 232962, the alkali metal content of the composition may be supplemented by further addition thereof, or reduced, for example by washing, at any subsequent point in the preparative process.

In step (B) of EPAs Nos. 0211577, 0232962 and 0169743, the precipitate obtained in step (A) is recovered. This may suitably be accomplished by filtration but other methods for separating solids from liquids, for example centrifugation, may be employed. After recovery it is preferred to wash the precipitate, suitably with water, so as to remove unwanted residual soluble matter. As per EPAs Nos. 0232962 and 0169743 it is also preferred to dry the precipitate, suitably at a temperature below 180° C., for example about 100° to 150° C., and in EPA No. 0211577, suitably at an elevated temperature below 150° C., e.g., 120° C. And, as per EPAs Nos. 0232962 and 0169743, it is possible that some thermal decomposition may occur in the drying step.

Thermally decomposable compounds comprised in the precipitate recovered in step (B) of EPAs Nos. 0169743 and 0232962 are preferably further thermally decomposed in a discrete step (C); and, in step (C) of EPA No. 0211577, thermally decomposable compounds comprised in the mixture obtained in step (B) are thermally decomposed. This may suitably be accomplished by heating the precipitate, suitably in a non-reducing atmosphere, for example a stream of inert gas, such as nitrogen as per EPAs 0169743, 0232962 and 0211577, or an oxygen-containing gas such as air as per EPA No. 0211577, at a temperature suitably in the range from 150° to 600° C. for EPA No. 0232962 and 250° to 600° C. for that of EPAs Nos. 0169743 and 0211577.

In order to convert the compositions of formulae (I) and (I)$_1$ of EPAs Nos. 0169743, 0232962 and 0211577 into a catalyst for use in the conversion of syngas to hydrocarbons having a carbon number greater than 1, it is generally necessary to reductively activate the composition, suitably by contact at elevated temperature with a reducing gas, for example hydrogen, carbon monoxide or mixtures thereof. A suitable reducing gas is for example hydrogen which may be diluted with an inert gas such as argon or nitrogen as per EPA No. 0811577. Typically, the conditions employed may suitably be: for EPAs Nos. 0232962, 0169743 and 0211577, a pressure in the range from 1 to 100 bar; for EPA No. 0232962 a temperature in the range from 150° to 600° C.; for EPA No. 0169743 a temperature in the range from 150° to 350° C.; for EPA No. 0211577 a temperature in the range from 150° to 300° C. and, for all three EPAs for a period of up to 24 hours or longer. EPAs Nos. 0169743 and 0232962 state that reductive activation may be effected as a discrete step prior to use as a catalyst for the conversion of synthesis gas or it may be incorporated as a preliminary step into the synthesis gas conversion process with the latter being preferred in EPA No. 0232962; and in EPA No. 0211577 the discrete step is preferred while the reductive activation may also be incorporated into the synthesis gas conversion process and effected in situ.

Those skilled in the art will readily appreciate that it may be possible to combine the thermal decomposition step and the reductive activation step into a single step under certain circumstances.

It is believed that coprecipitated catalysts differ fundamentally from impregnated catalysts and that this difference is reflected in their catalytic performance.

EPAs Nos. 0169743, 0232962 and 0211577 also provide processes for the production of hydrocarbons having a carbon number greater than one from synthesis gas which process comprises contacting synthesis gas with a catalyst comprising a reductively activated composition having the respective formulae (I) or (I)$_1$ produced by the respective process at a temperature in the range from 190° to 400° C. and a pressure in the range from about 1 bar to 100 bar.

Reductive activation of the composition of formula (I) of either EPA Nos. 0169743 or 0232962 may be conducted either as a separate step outside the syngas conversion reactor, as a discrete step within the syngas conversion reactor prior to syngas conversion or within the syngas conversion reactor under syngas conversion conditions.

With regard to the process of EPA No. 0232962 benefits can arise from periodically treating the catalyst with hydrogen. This may suitably be accomplished by shutting off the carbon monoxide feed from time to time during the process.

As is well known in the art synthesis gas principally comprises carbon monoxide and hydrogen and possibly also minor amounts of carbon dioxide, nitrogen and other inert gases depending upon its origin and degree of purity. Methods for preparing synthesis gas are established in the art and usually involve the partial oxidation of a carbonaceous substance, e.g. coal. Alternatively, synthesis gas may be prepared, for example by the catalytic steam reforming of methane. For the purpose of EPAs Nos. 0169743, 0232962 and 0211577, the carbon monoxide to hydrogen ratio may suitably be in the range from 2:1 to 1:6. Whilst the ratio of the carbon monoxide to hydrogen in the synthesis gas produced by the aforesaid processes may differ from these ranges, it may be altered appropriately by the addition of either carbon monoxide or hydrogen, or may be adjusted by the so-called shift reaction well known to those skilled in the art.

In a modification of the processes for the production of hydrocarbons of EPAs Nos. 0169743, 0232962 and 0211577 there may be combined with the catalyst an inert material, for example silica. In the processes of EPAs Nos. 0169743 and 0211577 it is preferred to combine the catalyst with a zeolite.

In a preferred embodiment in the process of EPA No. 0232962, the catalyst may be combined with an acidic component, for example either a zeolite or pillared clay.

The zeolite or pillared clay may be either physically admixed with the composition to form an intimately mixed bed or may be separate therefrom, for example in the form of a split bed, the zeolite or pillared clay forming one portion of the bed and the catalyst another. In the case of a physical admixture, the zeolite or pillared clay may be mixed with the composition either before or after reductive activation. Alternatively, the respective coprecipitation (step A) in the process for producing the respective composition of formulae (I) or (I)$_1$ may be performed in the presence of the zeolite or pillared clay, particularly when the precipitant is ammonium carbonate and/or bicarbonate and/or hydroxide.

A suitable zeolite is an MFI-type zeolite, for example ZSM-5 as described in U.S. Pat. No. 3,702,886, though as per EPA No. 0232962 other suitable high silica crystalline alumino- or gallo-silicate zeolites may be employed.

In the processes of EPAs Nos. 0169743 and 0211577, it is preferred to use the hydrogen form of the zeolite which may be obtained by acid exchange or by thermal decomposition of the ammonium-exchanged form of the zeolite. Preferably the alkali metal-free composition (b in the formula (I)=0) is modified by combination with the zeolite. Suitably the ratio of the number of parts by volume of catalyst composition to the number of parts by volume of the zeolite may be in the range from 5:1 to 1:5, preferably about 2:1. Combination with a zeolite can improve the selectivity to gasoline range paraffinic hydrocarbons. In EPA No. 0211577, combination with a zeolite can improve selectivity to gasoline range paraffinic hydrocarbons.

Suitable pillared clays are described for example in GB-A No. 2,059,408, U.S. Pat. No. 4,216,188, U.S. Pat. No. 4,248,739, U.S. Pat. No. 4,515,901 and U.S. Pat. No. 4,367,163. A particularly suitable pillared clay is the silylated pillared clay described in our co-pending EP-A No. 0150898. The aforesaid patent publications are incorporated by reference herein.

The temperature in the processes of EPAs Nos. 0169743, 0232962 and 0211577 is preferably in the range from 250° to 350° C. and the pressure is preferably in the range from 10 to 50 bars. The GHSV may suitably be, as per EPA No. 0232962, in the range from 100 to 2,000 h$^{-1}$, and, as per EPAs Nos. 0169743 and 0211577 in the range from 100 to 5,000 h$^{-1}$.

The processes of EPAs Nos. 016974, 0232962 and 0211572 may be carried out batchwise or continuously in a fixed bed, fluidised bed, moving bed or slurry phase reactor.

DISCUSSION OF PRESENT INVENTION CONTINUED

Preferred Fischer-Tropsch catalysts are those which are tolerant to carbon dioxide, in which case step (C') may be eliminated or substantially reduced in size.

Thereafter it is preferred to separate the gaseous hydrocarbon fraction from the liquid hydrocarbon fraction of the F-T product and remove water therefrom. This may be accomplished by conventional means. Conveniently this separation may be combined with the separation of LPG from natural gas to provide the feedstock for step (A) of the process. The liquid C$_5$+ hydrocarbon fraction may suitably be used as a gasoline blending component.

In the event that the process is operated in proximity to a crude oil pipeline the BTX and liquid C$_5$+ hydrocarbon fraction may suitably be transported to the refinery via the crude oil pipeline.

BRIEF DESCRIPTION OF THE DRAWING

A preferred embodiment of the invention will now be described with reference to the accompanying FIG. 1 which takes the form of a flowsheet.

With reference to the FIG. 1, reference numeral 1 is a dehydrocyclodimerisation reaction and separation unit, 2 is a catalytic partial oxidation unit, 3 is a carbon dioxide separation unit, 4 is a Fischer-Tropsch conversion unit, 5 is a Fischer-Tropsch product separation unit and 6 to 17 are transfer lines.

In operation LPG separated from natural gas, is fed through line 6 to the unit 1 wherein it is contacted with a DHCD catalyst to produce BTX, methane and hydrogen, which are separated into BTX, a methane-rich gaseous fraction and a hydrogen-rich gaseous fraction, the BTX being recovered through line 7. The gaseous methane-rich fraction is passed through line 8, combined with methane from the LPG separation and fed via line 9 to the catalytic partial oxidation unit, oxygen and steam being fed through lines 10 and 11 respectively. In the catalytic partial oxidation unit 2 the feedstock is converted to a product comprising carbon monoxide and hydrogen, together with carbon dioxide and steam. The product is fed through line 12 to the separation unit 3, wherein carbon dioxide and water are removed.

The hydrogen-rich gaseous fraction from the DHCD unit 2 is transferred via line 14 and admixed with the substantially carbon dioxide and water-free synthesis gas existing from the separation unit through line 13, thereby raising the hydrogen to carbon monoxide molar ratio of the synthesis gas to a value of about 2.14:1, before the mixture enters the Fischer-Tropsch conversion unit 4. In the F-T unit 4 the synthesis gas is converted to water and hydrocarbons comprising a mixture of gaseous $C_2$-$C_4$ hydrocarbons and liquid $C_5+$ hydrocarbons, which mixture is passed through line 15 to an F-T product separation unit 5, wherein the product is separated into water, LPG which is recycled through line 16 to the LPG feed line 6, and a liquid $C_5+$ hydrocarbon fraction which is recovered through line 17. Although the F-T product separation unit 5 is shown as a separate unit in this case, it may be incorporated into the LPG from natural gas separation unit, thereby saving on plant.

It will be appreciated by those skilled in the art that the aforedescribed process may be modified whilst still retaining the essential character of the invention. For example, in addition to or as an alternative to step (D) synthesis gas could be converted either into methanol or a mixture of higher alcohols.

We claim:

1. A process for the production of aromatic hydrocarbons from a feedstock comprising ethane and/or propane and/or butane which process comprises the steps of:
   (A) reacting the feedstock in the presence of a dehydrocyclodimerisation catalyst to produce a product comprising aromatic hydrocarbons, hydrogen and methane,
   (B) separating the product of step (A) into an aromatic hydrocarbon fraction, a methane-rich gaseous fraction and a hydrogen-rich gaseous fraction,
   (C) feeding all or part of the methane-rich gaseous fraction separated in step (B) to a synthesis gas production unit, thereby to produce synthesis gas comprising hydrogen and carbon monoxide in a ratio less than or equal to 2:1, and
   (D) contacting the synthesis gas from step (C) together with all or part of the hydrogen-rich gaseous fraction separated in step (B), thereby increasing the hydrogen to carbon monoxide ratio of the synthesis gas to a value greater than 2:1, with a Fischer-Tropsch conversion catalyst to produce a hydrocarbon product.

2. A process according to claim 1 wherein the synthesis gas production unit is an oxidative synthesis gas production unit.

3. A process according to claim 1 wherein additional methane-containing hydrocarbon gas is fed to the synthesis gas production unit in step (C).

4. A process according to claim 1 wherein the feedstock reacted in step (A) is LPG separated from natural gas.

5. A process according to claim 4 wherein methane recovered from the separation of the LPG from natural gas is fed to step (C).

6. A process according to claim 1 wherein the dehydrocyclodimerisation catalyst of step (A) is a gallium loaded ZSM-5 type aluminosilicate zeolite.

7. A process according to claim 1 wherein the oxidative synthesis gas production unit of step (C) is either a catalysed or uncatalysed partial oxidation unit.

8. A process according to claim 2 wherein the partial oxidation unit is a catalytic partial oxidation unit which takes the form of either a fluidised bed or a spouted bed of reforming catalyst to which is fed the methane-containing feedstock, steam and an oxygen-containing gas.

9. A process according to claim 1 wherein carbon monoxide is produced in step (C) and in an additional step (C') carbon dioxide is removed from the synthesis gas.

10. A process according to claim 1 wherein the amount of hydrogen-rich gaseous fraction admixed with the synthesis gas in step (D) is sufficient to produce a hydrogen to carbon monoxide molar ratio greater than 2:1.

11. A process according to claim 10 wherein the hydrogen to carbon monoxide molar ratio is in the range from 2.05 to 2.2:1.

12. A process according to claim 1 wherein the Fischer-Tropsch catalyst comprises ruthenium and ceria.

13. A process according to claim wherein the Fischer-Tropsch catalyst further incorporates a zeolite.

14. A process according to claim 1 wherein the Fischer-Tropsch catalyst is one capable of converting synthesis gas to waxy hydrocarbons.

15. A process according to claim 14 wherein the Fischer-Tropsch catalyst comprises cobalt and zinc oxide.

16. A process according to claim 15 wherein the Fischer-Tropsch catalyst further incorporates a zeolite.

* * * * *

UNITED STATES PATENT AND TRADEMARK OFFICE
CERTIFICATE OF CORRECTION

PATENT NO.  : 4,806,699
DATED       : February 21, 1989
INVENTOR(S) : David J.H. Smith and William T. Woodfin It is certified that error appears in the above-identified patent and that said Letters Patent is hereby corrected as shown below:

Col. 3, l. 12, should read "...especially preferable..."

Col. 5, l. 30, the word "supra" should be underlined.

Col. 9, l. 33, should read "... LHSV of 1 to 10..."

Col. 10, l. 4, should read "...comprising subjecting..."

Col. 10, l. 47, should read "of the silicas is less..."

Col. 10, l. 65, should read "...produce these catalysts..."

Col. 14, l. 61, should read "...from an LPG..."

Col. 15, l. 1, should read "...No. 2179366 (BP Case No. 6046)..."

Col. 17, l. 18, should read "...the nozzle is..."

Claim 13, l. 1, after "claim" and before "wherein" intert --12--.

Signed and Sealed this

Thirtieth Day of January, 1990

*Attest:*

JEFFREY M. SAMUELS

*Attesting Officer*     *Acting Commissioner of Patents and Trademarks*

UNITED STATES PATENT AND TRADEMARK OFFICE
CERTIFICATE OF CORRECTION

PATENT NO. : 4,806,699
DATED : February 21, 1989
INVENTOR(S) : David J.H. Smith and William T. Woodfin It is certified that error appears in the above-identified patent and that said Letters Patent is hereby corrected as shown below:

Col. 3, l. 12, should read "...especially preferable..."

Col. 5, l. 30, the word "supra" should be underlined.

Col. 9, l. 33, should read "... LHSV of 1 to 10..."

Col. 10, l. 4, should read "...comprising subjecting..."

Col. 10, l. 47, should read "of the silicas is less..."

Col. 10, l. 65, should read "...produce these catalysts..."

Col. 14, l. 61, should read "...from an LPG..."

Col. 15, l. 1, should read "...No. 2179366 (BP Case No. 6046)..."

Col. 17, l. 18, should read "...the nozzle is..."

Claim 13, l. 1, after "claim" and before "wherein" intert --1--.

This certificate supersedes Certificate of Correction issued January 30, 1990.

Signed and Sealed this

Tenth Day of April, 1990

Attest:

HARRY F. MANBECK, JR.

Attesting Officer

Commissioner of Patents and Trademarks